(12) United States Patent
Weizman

(10) Patent No.: US 8,715,277 B2
(45) Date of Patent: May 6, 2014

(54) CONTROL OF JAW COMPRESSION IN SURGICAL INSTRUMENT HAVING END EFFECTOR WITH OPPOSING JAW MEMBERS

(75) Inventor: Patrick A. Weizman, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 680 days.

(21) Appl. No.: 12/963,001

(22) Filed: Dec. 8, 2010

(65) Prior Publication Data

US 2012/0150176 A1    Jun. 14, 2012

(51) Int. Cl.
*A61B 18/04*    (2006.01)
(52) U.S. Cl.
USPC .................................. 606/27; 606/51; 606/52
(58) Field of Classification Search
USPC ............... 606/27, 34, 41, 51–52, 208; 81/318
See application file for complete search history.

(56) References Cited

U.S. PATENT DOCUMENTS

| | | | |
|---|---|---|---|
| 2,366,274 A | 1/1945 | Luth et al. | |
| 2,458,152 A | 1/1949 | Eakins | |
| 2,510,693 A | 6/1950 | Green | |
| 3,166,971 A | 1/1965 | Stoecker | |
| 3,580,841 A | 5/1971 | Cadotte et al. | |
| 3,703,651 A | 11/1972 | Blowers | |
| 3,777,760 A * | 12/1973 | Essner | 604/1 |
| 4,005,714 A | 2/1977 | Hiltebrandt | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,545,926 A | 10/1985 | Fouts, Jr. et al. | |
| 4,550,870 A | 11/1985 | Krumme et al. | |
| 4,582,236 A | 4/1986 | Hirose | |
| 4,761,871 A | 8/1988 | O'Connor et al. | |

(Continued)

FOREIGN PATENT DOCUMENTS

| | | |
|---|---|---|
| DE | 29623113 U1 | 10/1997 |
| DE | 20004812 U1 | 9/2000 |

(Continued)

OTHER PUBLICATIONS

U.S. Appl. No. 12/911,943, filed Oct. 26, 2010.

(Continued)

*Primary Examiner* — Michael Peffley
*Assistant Examiner* — Daniel Fowler

(57) ABSTRACT

A surgical instrument comprising a surgical instrument with opposing jaw members for clamping tissue therebetween. The surgical instrument may comprise a latch at a distal end of the end effector. The latch latches the distal end of the first jaw member to the distal end of the second jaw when the jaw members are in the closed position. Also, one of the jaw members may comprise a moveable tissue-contacting portion and a thermally-controlled spring adjacent to the tissue-contacting portion. The thermally-controlled spring is transitionable between a contracted state and an expanded state. The thermally-controlled spring may comprise a temperature-dependent, two-way memory effect, shape memory material. In the expanded state, the thermally-controlled spring urges the moveable tissue-contacting portion in a direction toward the other jaw member when the jaw members are in the closed position.

16 Claims, 7 Drawing Sheets

(56) References Cited

U.S. PATENT DOCUMENTS

| | | |
|---|---|---|
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A | 3/1993 | Abele et al. |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,520,704 A * | 5/1996 | Castro et al. .................. 606/208 |
| 5,522,839 A | 6/1996 | Pilling |
| 5,558,671 A | 9/1996 | Yates |
| 5,563,179 A | 10/1996 | Stone et al. |
| 5,571,121 A * | 11/1996 | Heifetz .......................... 606/158 |
| 5,599,350 A | 2/1997 | Schulze et al. |
| 5,618,307 A | 4/1997 | Donlon et al. |
| 5,624,452 A | 4/1997 | Yates |
| 5,647,871 A | 7/1997 | Levine et al. |
| 5,662,667 A * | 9/1997 | Knodel .......................... 606/151 |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,174,309 B1 * | 1/2001 | Wrublewski et al. ........... 606/45 |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,252,667 B2 | 8/2007 | Moses et al. |
| 7,267,685 B2 | 9/2007 | Butaric et al. |
| 7,287,682 B1 | 10/2007 | Ezzat et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |

(56) References Cited

U.S. PATENT DOCUMENTS

| | | | |
|---|---|---|---|
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 * | 6/2011 | Lindquist ............................ 433/4 |
| 7,981,113 B2 | 7/2011 | Truckai et al. |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,282,669 B2 | 10/2012 | Gerber et al. |
| 8,298,232 B2 | 10/2012 | Unger |
| 8,323,310 B2 | 12/2012 | Kingsley |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0107784 A1 * | 5/2005 | Moses et al. ...................... 606/51 |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0179476 A1 * | 8/2007 | Shelton et al. ...................... 606/1 |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0138003 A1 | 5/2009 | Deville et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0136353 A1 | 5/2012 | Romero |
| 2013/0023875 A1 | 1/2013 | Harris et al. |
| 2013/0053831 A1 | 2/2013 | Johnson et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |

(56) References Cited

FOREIGN PATENT DOCUMENTS

| | | |
|---|---|---|
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/089717 A1 | 7/2011 |
| WO | WO 03/001986 A2 | 1/2013 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . ., accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/841,480, filed Jul. 22, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.

(56) References Cited

OTHER PUBLICATIONS

U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
International Search Report for PCT/US2011/063732, Jun. 29, 2012 (7 pages).
Wright, et al., "Time-Temperature Equivalence of Heat-Induced Changes in Cells and Proteins," Feb. 1998. ASME Journal of Biomechanical Engineering, vol. 120, pp. 22-26.

* cited by examiner

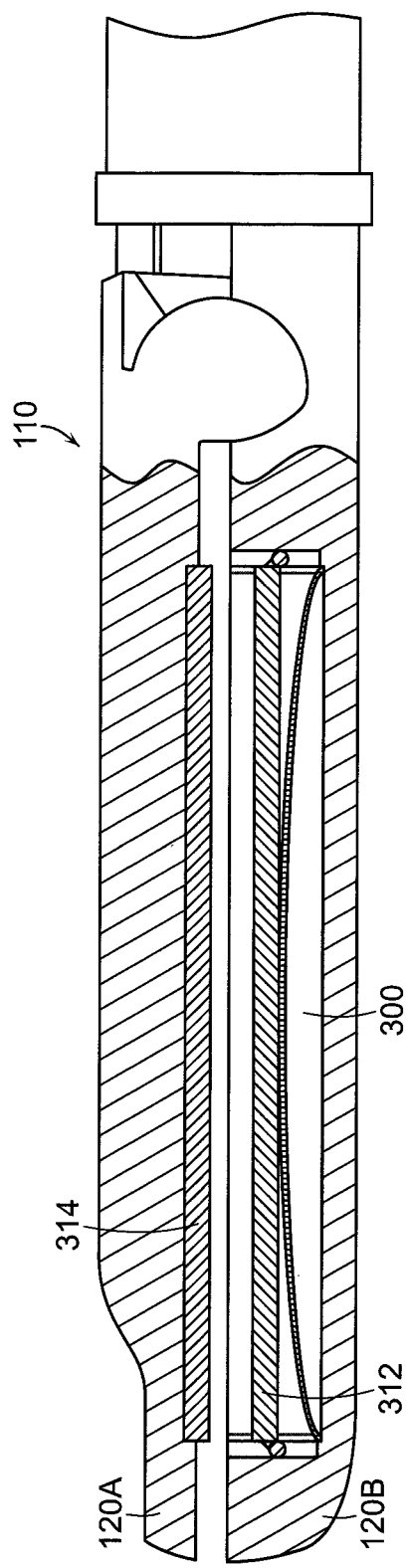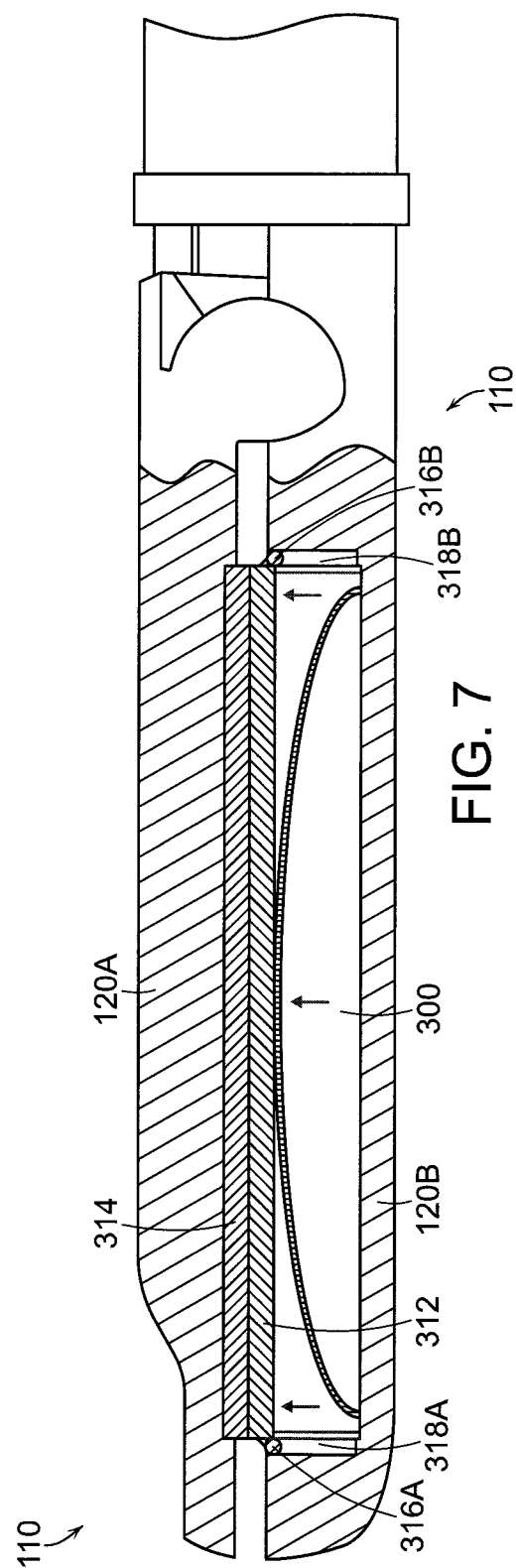

CONTROL OF JAW COMPRESSION IN SURGICAL INSTRUMENT HAVING END EFFECTOR WITH OPPOSING JAW MEMBERS

BACKGROUND

Many surgical devices comprise end effectors with opposing jaw members that are capable of opening and closing. The jaw members grip tissue therebetween when the jaw members are in the closed position. Many such devices are hand-powered, whereby the operator retracts a closure trigger to cause the jaw members to transition to the closed position, and releases the closure trigger to cause the jaw members to transition to the open position. Other types of surgical devices use electrical or pneumatic motors to close the jaw members.

In surgical procedures utilizing such devices, controlling the compression by the jaw members is important if not critical to the success of the procedure: generally the better the compression can be controlled, the more successful the procedure will be.

SUMMARY

In one general aspect, the present invention is directed to a surgical instrument with opposing jaw members for clamping tissue therebetween, where the compression by the opposing jaw members on the tissue is more controllable, reliable, and consistent. In one embodiment, the surgical instrument comprises a latch at a distal end of the end effector. The latch latches the distal end of the first jaw member to the distal end of the second jaw when the jaw members are in the closed position. By latching the jaw members together, preferably at their distal ends, the tendency of the jaw members to deflect when the surgical instrument is actuated is reduced, thereby maintaining the compression force along the axial length of the jaw members throughout the actuation time period of the end effector.

In another general respect, the present invention is directed to a surgical instrument with opposing jaw members, where one of the jaw members comprises a moveable tissue-contacting portion and a thermally-controlled spring adjacent to the tissue-contacting portion. The thermally-controlled spring is transitionable between a contracted state and an expanded state. The thermally-controlled spring may comprise a temperature-dependent, two-way memory effect, shape memory material. In the expanded state, the thermally-controlled spring urges the moveable tissue-contacting portion in a direction toward the other jaw member, thereby providing greater tissue compression when the jaw members are in the closed position. In, for example, RF or ultrasonic end effectors, the thermally-controlled spring may be heated, such that it transitions to the expanded state, from the RF or ultrasonic energy in the end effector. This way, consistent compression forces on the clamped tissue can be maintained through the procedure, e.g., throughout the application of the RF or ultrasonic energy. Alternatively, passive heaters could be used in a controlled manner to heat the thermally-controlled spring.

FIGURES

Various embodiments of the present invention are described herein by way of example in conjunction with the following figures, wherein:

FIGS. 6 and 7 illustrate an end effector with a thermally-controlled spring according to various embodiments of the present invention.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Figure 1:
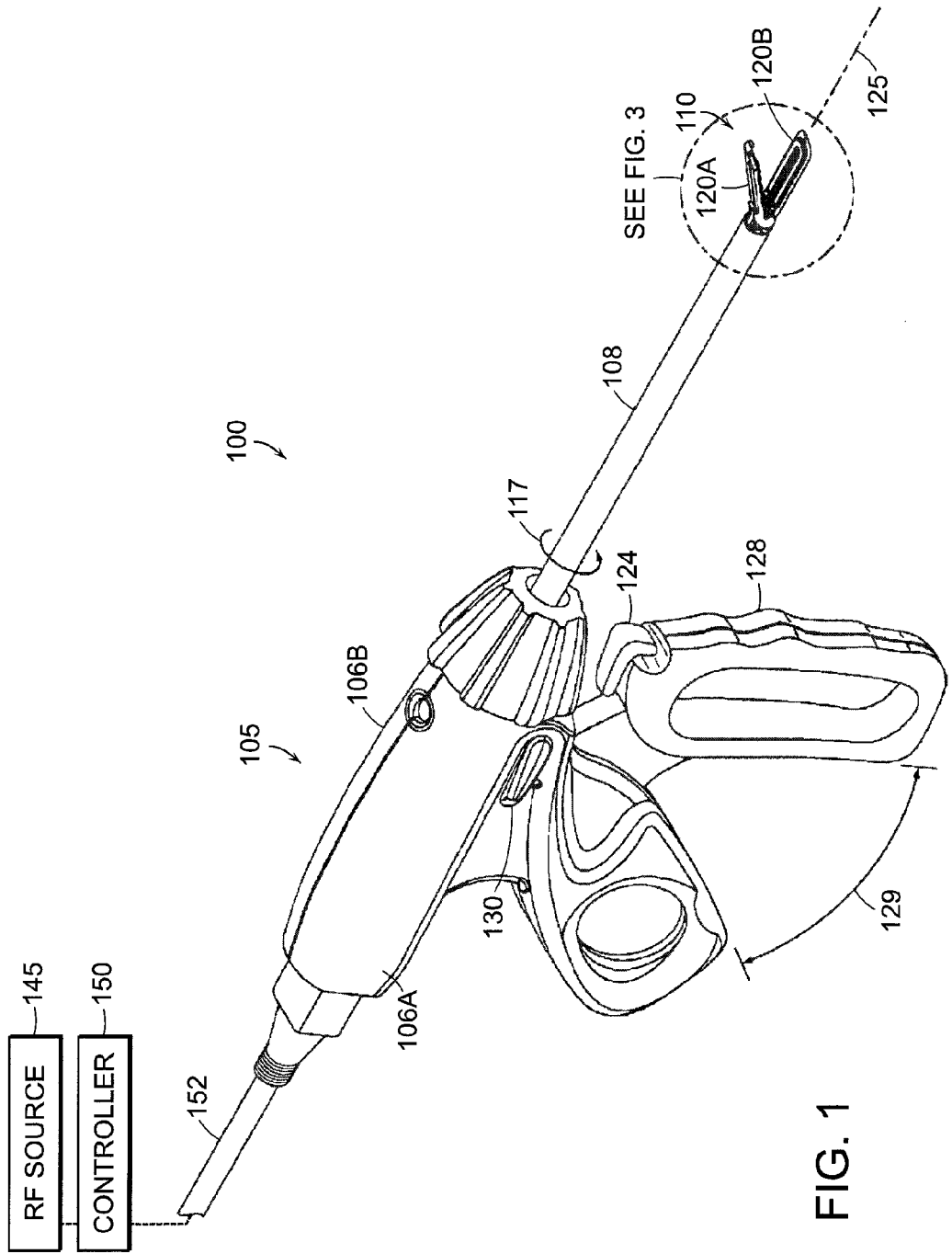
FIGS. 1-5 and 8 illustrate one type of surgical device that may implement embodiments of the present invention.
Figure 2:
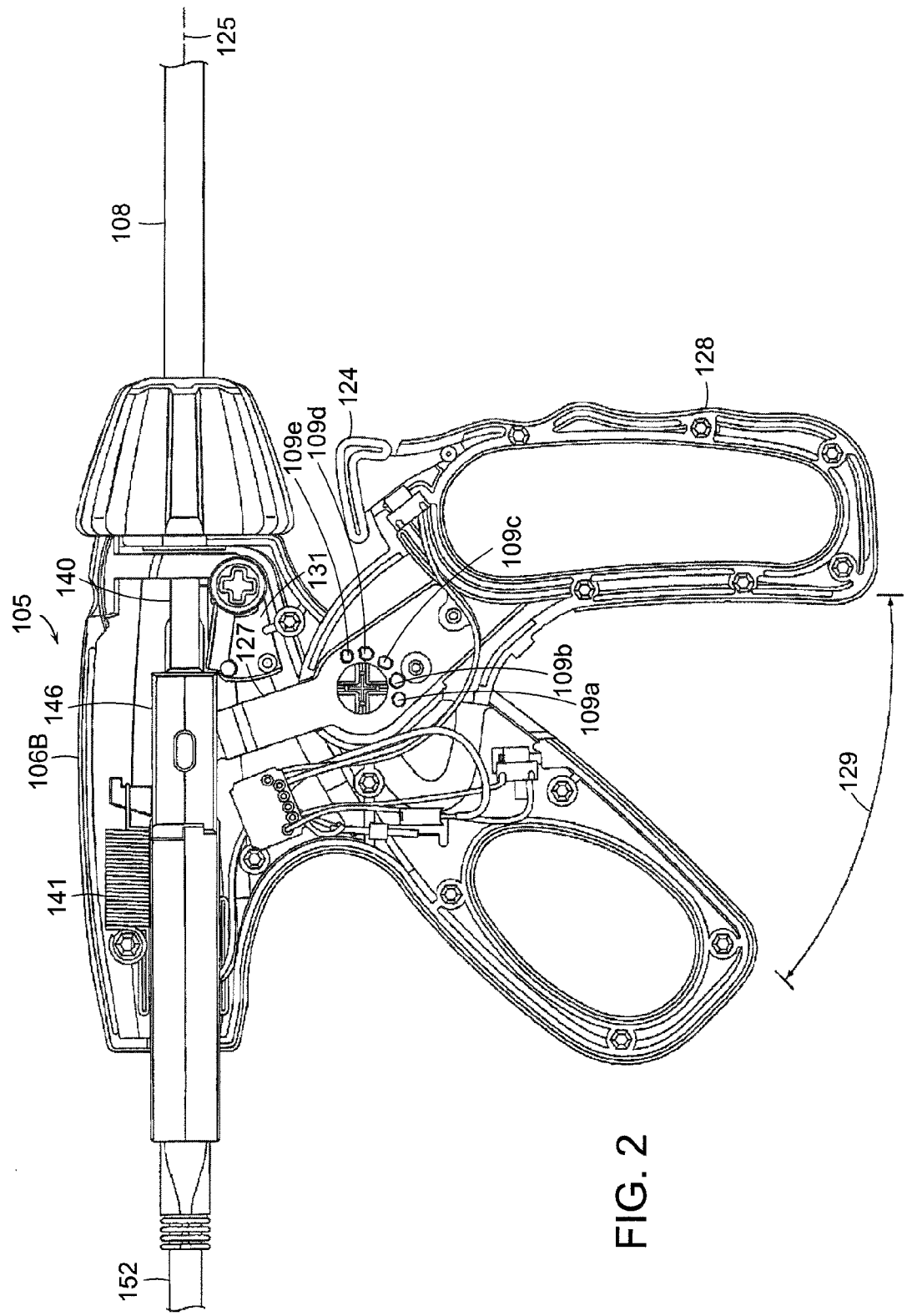

In one general aspect, the present invention is directed to any type of surgical device having an end effector with at least two opposing jaw members for gripping or positioning tissue therebetween, and where the jaw compression is controlled by one or more of the techniques disclose herein. FIGS. 1-2 illustrate one type of surgical device 100 that may implement embodiments of the present invention. The illustrated device 100 is configured for transecting captured tissue positioned between the jaw members and for contemporaneously welding the captured tissue margins with controlled application of RF energy. Although the device 100 uses RF energy to weld the tissue margins, the present invention is not so limited and other mechanisms could be used for fastening the tissue in other embodiments, such as staples, harmonics, adhesives, etc. In addition, embodiments of the present invention could be used in a clamping device, such as various types of hemostats or other types of grippers. As shown in the example of FIGS. 1-2, the device 100 can comprise a proximal handle 105, a distal working end or end effector 110, and an introducer or elongate shaft 108 disposed in-between. End effector 110 may comprise a set of openable-closeable jaw members with straight or curved jaws: an upper first jaw 120A and a lower second jaw 120B. First jaw 120A and second jaw 120B may be coupled to an electrical source or RF source 145 and a controller 150 through electrical leads in cable 152. Controller 150 may be used to activate electrical source 145.

FIG. 2 is a side view of the handle 105 of device 100, shown with half of a first handle body 106A (see FIG. 1) removed to illustrate some of the components within second handle body 106B. Handle 105 may comprise a lever arm 128 that may be pulled along a path 129. Lever arm 128 may be coupled to a movable cutting member 140 disposed within elongate shaft 108 by a shuttle 146 operably engaged to an extension 127 of lever arm 128. The shuttle 146 may further be connected to a biasing device, such as spring 141, which may also be connected to the second handle body 106B, to bias the shuttle 146 and thus the cutting member 140 in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers, or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms, for example, cutting member 140, for actuating the jaws and for carrying electrical leads for delivery of electrical energy to electrosurgical components of end effector 110.

End effector 110 may be adapted for capturing (or clamping), welding, and transecting tissue in various embodiments. First jaw 120A and second jaw 120B may close to thereby capture, clamp, or engage tissue about a longitudinal axis 125 defined by cutting member 140. First jaw 120A and second jaw 120B may also apply compression to the tissue. Elongate shaft 108, along with first jaw 120A and second jaw 120B, can be rotated a full 360° degrees, as shown by arrow 117, relative to handle 105 through, for example, a rotary triple contact. First jaw 120A and second jaw 120B can remain openable and/or closeable while rotated.

Figure 3:
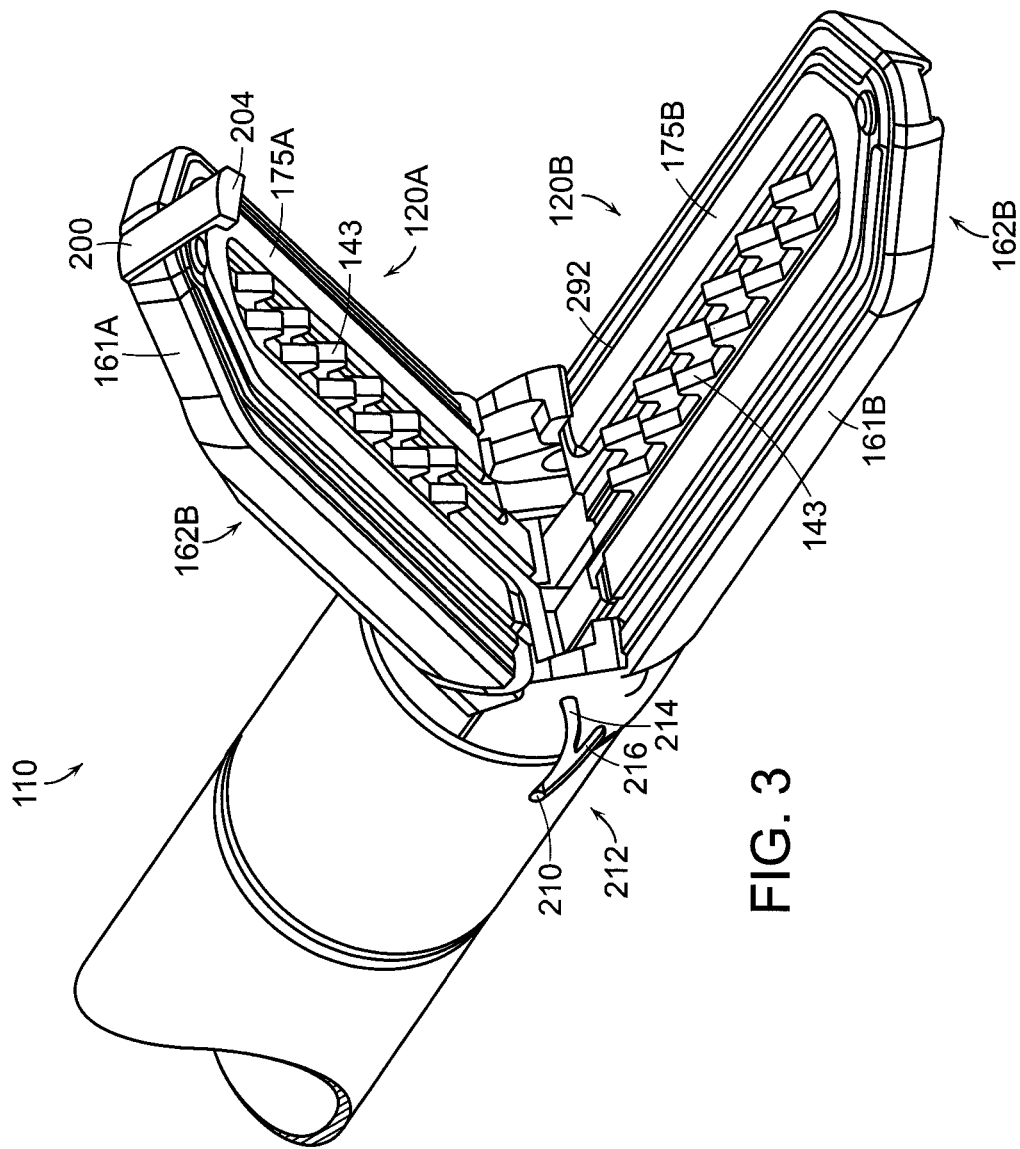
Figure 4:
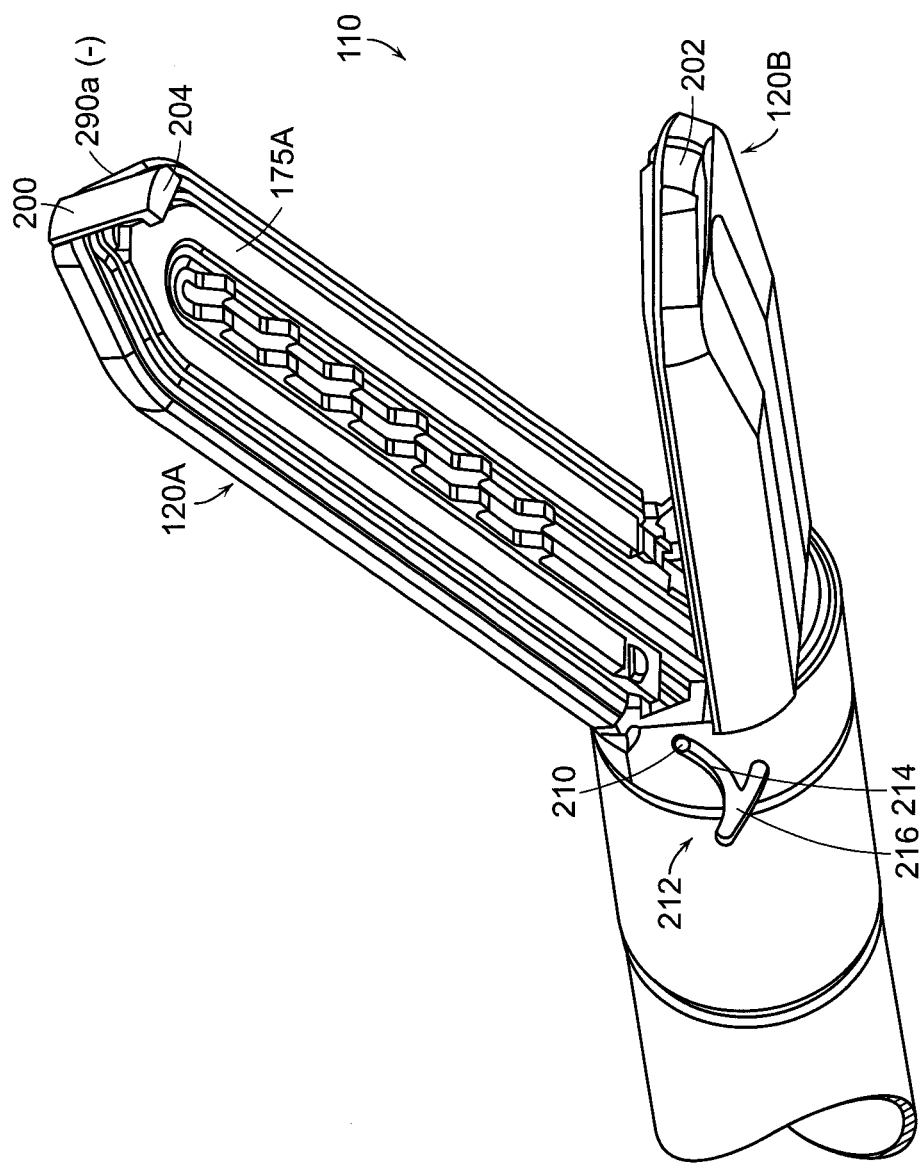
Figure 5:
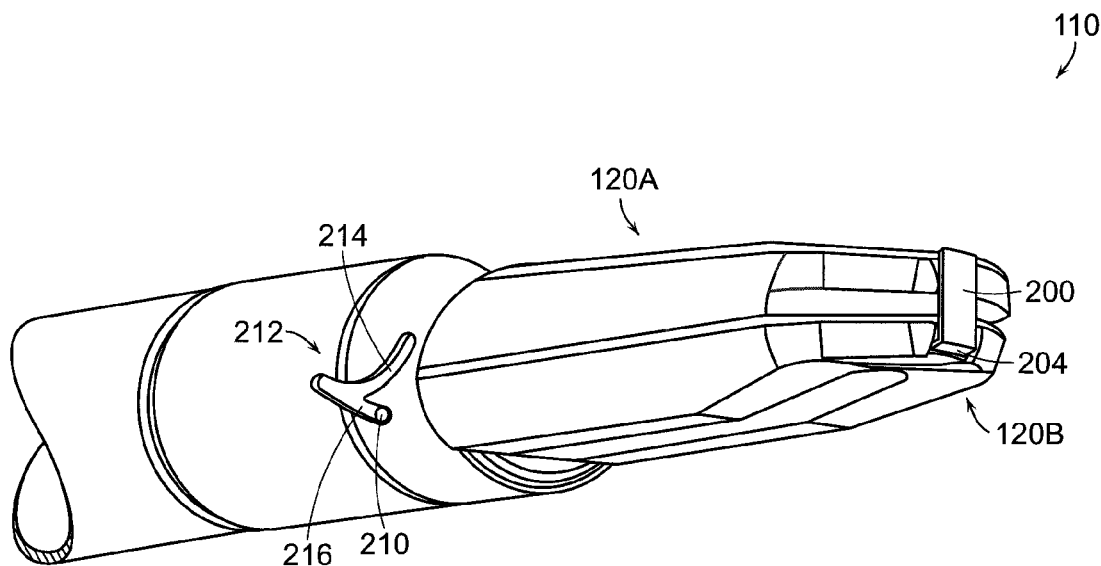

The jaw members of the end effector 110 are transitionable between open and closed positions, as shown in FIGS. 3-5, which are perspective views of end effector 110 in the open and closed positions, respectively. In various embodiments, the first jaw 120A and second jaw 120B may each have tissue-gripping elements, such as teeth 143, disposed on the inner portions of first jaw 120A and second jaw 120B. First jaw 120A may comprise an upper first jaw body 161A with an upper first outward-facing surface 162A and an upper first energy delivery surface 175A. Second jaw 120B may comprise a lower second jaw body 161B with a lower second outward-facing surface 162B and a lower second energy delivery surface 175B. First energy delivery surface 175A and second energy delivery surface 175B may both extend in a "U" shape about the distal end of end effector 110.

Figure 8:
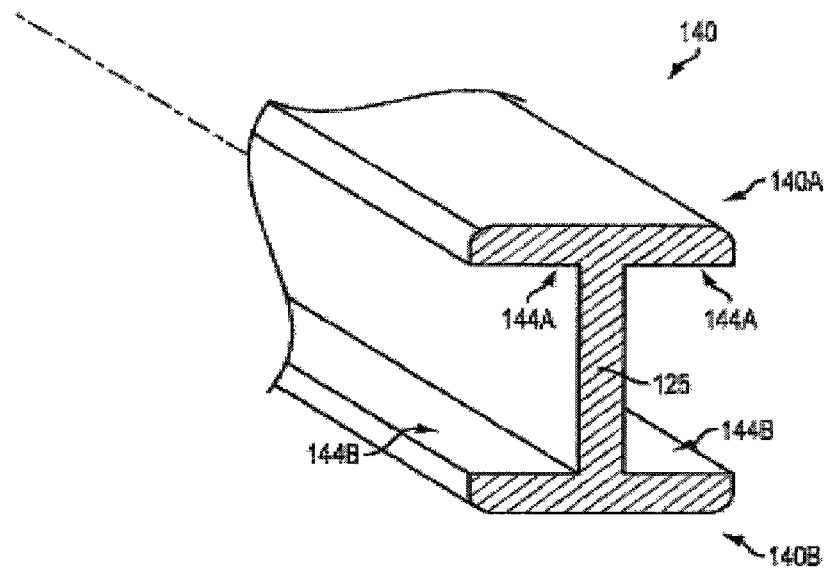

Referring briefly now to FIG. 8, a portion of cutting member 140 is shown. The lever arm 128 of handle 105 (see FIG. 2) may be adapted to actuate cutting member 140, which also functions as a jaw-closing mechanism. For example, cutting member 140 may be urged distally as lever arm 128 is pulled proximally along path 129 via shuttle 146, seen in FIG. 2 and discussed above. The cutting member 140 may comprise one or several pieces, but in any event, may be movable or translatable with respect to the elongate shaft 108 and/or jaws 120A, 120B. In addition, in at least one embodiment, the cutting member 140 may be made of 17-4 precipitation hardened stainless steel. The distal end of cutting member 140 may comprise a flanged "I"-beam configured to slide within channels in the jaws 120A and 120B, as disclosed in U.S. patent application Ser. No. 12/911,943, which is incorporated herein by reference. Cutting member 140 may slide within the channels in the jaw members 120A-B to open and close first jaw 120A and second jaw 120B. The distal end of cutting member 140 may also comprise upper flange or "c"-shaped portion 140A and lower flange or "c"-shaped portion 140B. The flanges 140A and 140B respectively define inner cam surfaces 144A and 144B for engaging outward facing surfaces of first jaw 120A and second jaw 120B. The opening-closing of jaws 120A and 120B can apply compressive forces on tissue using cam mechanisms which may include reciprocating "I-beam" cutting member 140 and the outward facing surfaces 162A, 162B of jaws 120A, 120B.

Referring now to FIGS. 1 and 3, end effector 110 may be coupled to electrical source 145 and controller 150. First energy delivery surface 175A and second energy delivery surface 175B may likewise each be coupled to electrical source 145 and controller 150. First energy delivery surface 175A and second energy delivery surface 175B may be configured to contact tissue and delivery electrosurgical energy to engaged tissue, which is adapted to seal or weld the tissue. Controller 150 can regulate the electrical energy delivered by electrical source 145, which in turn delivers electrosurgical energy to first energy-delivery surface 175A and second energy-delivery surface 175B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. Further, the opposing first and second energy delivery surfaces 175A and 175B may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,354,440; 7,381,209; 7,311,709; 7,309,849; 7,220,951; 7,189,233; 7,186,253; 7,169,156; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 5A:
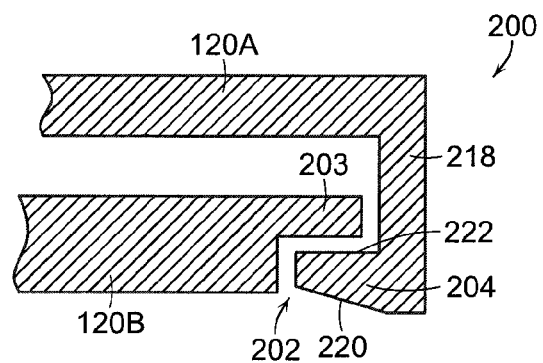
FIG. 5A illustrates a latch of an end effector according to various embodiments of the present invention.

As shown in FIGS. 3-5, the distal end of one of the jaw members, such as first jaw 120A, may comprise a downwardly extending tab 200. The other jaw member, e.g., the second jaw 120B, may have a corresponding slot or opening 202 under an extended portion 203 of the lower jaw 120B for receiving the tab 200 when the jaw members are in the closed position, as shown in FIG. 5. As shown in FIG. 5 and the more detailed view of the tab 200 in FIG. 5A, the tab 200 may comprise a locking leg 218 and a protrusion or lip 204. The locking leg 218 may extend downwardly from the upper jaw 120A and the lower lip 204 may extend from the locking leg 218 generally perpendicularly proximately (toward the handle). The lip 204 may comprise a lower cam surface 220 and an upper locking surface 222. When the jaw members 120A-B transition from an open position to the closed position, the lower cam surface 220 engages the extended portion 203 of the lower jaw 120B until the cam surface 220 passes the extended portion 203, at which point the lip 204 slides into the lower jaw opening 202, thereby latching the upper and lower jaw members 120A-B, in the process providing higher compression for the tissue clamped within the jaw members 120A-B when the device is actuated. For example, in prior art devices, as the cutting instrument travels from the proximate to the distal end of the end effector, the compression at the distal end of the end effector tends to lessen because the jaw members tend to deflect. In the embodiment of FIGS. 3-5, however, by latching the jaw members 120A-B at the distal end, the tendency of the jaw members 120A-B to deflect when the device is actuated is reduce, thereby maintaining the compression force along the axial length of the end effector 110.

According to various embodiments, as shown in FIGS. 3-5, the upper jaw 120A may comprise a pin 210 that follows a cam slot 212 to transition the upper jaw 120A between the open and closed positions. The lower jaw 120B may remain stationary. In the open position, as shown in FIG. 4, the pin 210 may be at a forward position in an upper lobe 214 of the cam slot 212. When closing the jaw members 120A-B, upon retraction of the lever arm 128, the pin 210 may slide down the upper lobe 214 and then forward in a lower lobe 216 of the cam slot 212 to a lower, forward position, as shown in FIG. 5. In the forward position, upper jaw 120A moves forward so that the lip 204 of the tab 200 may extend into the recess 202 of the lower jaw 120B. When the jaw members 120A-B are opened, the pin 210 may slide up and back the lower lobe 216 of the cam slot 212, as shown in FIG. 3, allowing the upper jaw 120A to unlatch, and then slide up the upper lobe 214 of the cam slot 212, as shown in FIG. 4, to the open position.

Although the above embodiment was described in the context of a RF surgical instrument, a similar type latch for latching the distal ends of the jaw members 120A-B could be used in other types of surgical instruments having openable-closeable jaw members, such as endoscopic staplers and ultrasonic devices. More details regarding endoscopic staplers may be found in U.S. published patent applications Pub. No. 2009/0206124 A1 and Pub. No. 2009/0206140 A1, which are incorporated herein by reference in their entirety. More details regarding ultrasonic devices may be found in U.S. published patent applications Pub. No. 2010/0036405 A1, which is incorporated herein by reference in its entirety. An endoscopic stapler typically includes a staple cartridge in the end effector.

FIGS. 6-7 illustrate another embodiment of the present invention for controlling jaw compression. In the illustrated embodiment, one of the jaw members, such as lower jaw 120B, comprises a thermally controlled spring 300. The thermally controlled spring 300 may extend most of the length of the end effector 110, as shown in FIGS. 6-7. The thermally controlled spring 300 may comprise, in various embodiments, a temperature-dependent, two-way memory effect, shape memory material, such as a shape memory alloy, including but not limited to copper-zinc-aluminum-nickel, copper-aluminum-nickel, and/or nickel-titanium (NiTi) alloys. FIG. 6 shows the spring 300 in the cold or constructed position. When the spring 300 is heated above its cold-hot transition temperature, it assumes an expanded shape as shown in FIG. 7. When it is cooled below its hot-cold transition temperature (which may be a different temperature than the cold-hot transition temperature), it assumes its contracted shape as shown in FIG. 6.

In various embodiments, the spring 300 may be located under a moveable pad or tissue-contacting portion 312 in the lower jaw 120B. The pad 312 may face a corresponding tissue-contacting portion 314 in the upper jaw 120A. In some embodiments, the tissue-contacting portions 312, 314 may comprise, for example, opposing RF energy deliver surfaces. In other embodiments, one of the tissue-contacting portions, e.g., the lower pad 312, may comprise a blade of an ultrasonic surgical instrument (such as disclosed in U.S. published patent application Pub. No. 2010/0036405 A1) and the other tissue-contacting portions, e.g. pad 314, may be the clamp or jaw for the ultrasonic end effector.

The pad 312 may moveable up and down upon expansion and contraction of the spring 300, respectively. In addition, preferably the pad moves up and down generally evenly; that is, one end does not rise much higher or lower than the other, in order to provide more uniform compression over the length of the end effector 110. Any suitable mechanism for allowing the pad 312 to move up and down upon expansion/contraction of the spring 300 may be used. In various embodiments, as shown in the example of FIGS. 6-7, each end of the pad 312 may comprise a sled 316A, 316B that slides up and down in vertical tracks 318A, 318B defined in the lower jaw 120B. When the spring 300 is heated to its expanded shape, as shown in FIG. 7, the pads 312-314 are closer together than when the spring 300 is in its contracted shape, as shown in FIG. 6.

In operation, any suitable means for heating the spring 300 so that it transitions from its contracted shape (FIG. 6) to its expanded shape (FIG. 7) may be used. For example, when used in a RF instrument, heat from the RF electrodes in the end effector 110 may raise the temperature of the spring 300 above its cold-hot transition temperature so that the spring 300 assumes its expanded shape (FIG. 7). Discontinuance of delivery of the RF energy may allow the spring 300 to transition back to its contracted shape (FIG. 6). In an ultrasonic instrument, heat from the ultrasonic energy delivered by the end effector 100 may raise the temperature of the spring 300 above its cold-hot transition temperature so that the spring 300 assumes its expanded shape (FIG. 7). Discontinuance of delivery of the ultrasonic energy may allow the spring 300 to transition back to its contracted shape (FIG. 6). In other embodiments, resistive heaters adjacent to the spring 300 may be used to heat the spring 300. In such embodiments, actuation of the instrument may cause electrical current from a source (e.g., battery or other electricity power source) to run through the resistive heaters, to thereby heat the spring 300. Removal of the current from the resistive heaters may allow the spring 300 to transition back to its contracted shape.

In the embodiment shown in FIGS. 6-7, the spring 300 is positioned in the lower jaw 120B. In other embodiments, the spring 300 could be in the upper jaw 120A and/or both jaws 120A-B. Also, instead of one spring 300, there could be multiple springs in the lower and/or upper jaw members 120B, A.

The above described embodiments may be employed in any suitable surgical device comprising an opening-closing end effector with two jaw members moveable relative to each other, including, but not limited to bipolar RF surgical devices, harmonic devices (e.g., the jaw members may comprise one jaw and one blade in such embodiments), endo-cutters, clamps, etc. Also, a surgical instrument according to various embodiments of the present invention may include both the latching mechanism (see, e.g., FIGS. 1-5 and 5A) and the thermally-controlled spring (see, e.g., FIGS. 6-7).

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

In one general aspect, the present invention is directed to a surgical instrument that comprises an end effector having a distal end and a proximate end. The end effector comprises: (i) a first jaw member comprising a distal end and a proximate end; (ii) a second jaw member opposing the first jaw member, wherein the second jaw comprises a distal end and a proximate end, wherein the first jaw member is moveable relative to the second jaw member such that the jaw members are transitionable between an open position and a closed position; and (iii) a latch at a distal end of the end effector for latching the distal end of the first jaw member to the distal end of the second jaw when the jaw member are in a closed position.

In various implementations, the latch comprises a locking leg extending downwardly from the distal end of the first jaw member toward the second jaw member. The locking leg comprises a protrusion that slides into a recess at the distal end of the second jaw member when the first and second jaw members are in the closed position. The end effector may comprise at least one electrode, such as an RF electrode. The end effector may also comprise an ultrasonic end effector or a staple cartridge. The surgical instrument may also comprise a shaft connected to the end effector and a handle connected to the shaft. The handle may comprise a lever arm which, when actuated, causes the first and second jaw members to transition from the open position to the closed position.

In another general aspect, the present invention is directed to a surgical instrument comprising an end effector that has first and second opposing jaw members. The first jaw member is moveable relative to the second jaw member such that the jaw members are transitionable between an open position and a closed position and such that tissue can be clamped between the first and second jaw members when the first and second jaw members are in the closed position. The second jaw member comprises: (i) a moveable tissue-contacting portion; and (ii) a thermally-controlled spring adjacent to the tissue-contacting portion.

In various implementations, the thermally-controlled spring is transitionable between a contracted state and an expanded state, where the thermally-controlled spring urges the moveable tissue-contacting portion in a direction toward the first jaw member when the first and second jaw members are in the closed position and the thermally-controlled spring is in the expanded state. The thermally-controlled spring may comprise a temperature-dependent, two-way memory effect, shape memory material. For example, the thermally-controlled spring may comprise a shape memory alloy such as a copper-zinc-aluminum-nickel alloy, a copper-aluminum-nickel alloy, or a nickel-titanium alloy.

The tissue contacting portion may comprise at least one electrode, such as an RF electrode. Also, the end effector may comprise an ultrasonic end effector.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications, and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
an end effector comprising a distal end and a proximate end, wherein the end effector comprises:
   a first jaw member comprising a distal end and a proximate end, wherein the proximate end of the first jaw member comprises a pin;
   a second jaw member opposing the first jaw member, wherein the second jaw comprises a distal end and a proximate end, wherein the proximate end of the second jaw member comprises a multi-lobed cam slot with at least three lobes, wherein the pin of the first jaw member is disposed and moveable within the multi-lobed cam slot between the three lobes, wherein the first jaw member is moveable relative to the second jaw member such that the first and second jaw members are transitionable between an open position and a closed position, such that the first and second jaw members are in the open position when the pin of the first jaw member is in a first lobe of the multi-lobed cam slot and the first and second jaw members are in the closed position when the pin of the first jaw member is in a second lobe of the multi-lobed cam slot, and wherein the pin of the first jaw member moves into a third lobe of the multi-lobed cam slot when the pin transitions from the first lobe to the second lobe; and
a latch at a distal end of the end effector for latching the distal end of the first jaw member to the distal end of the second jaw member when the first and second jaw members are in the closed position.

2. The surgical instrument of claim 1, wherein the latch comprises a locking leg extending downwardly from the distal end of the first jaw member toward the second jaw member.

3. The surgical instrument of claim 2, wherein the locking leg comprises a protrusion that releasably slides into a recess at the distal end of the second jaw member when the first and second jaw members are in the closed position.

4. The surgical instrument of claim 1, wherein the end effector comprises at least one electrode.

5. The surgical instrument of claim 4, wherein the at least one electrode comprises at least one RF electrode.

6. The surgical instrument of claim 1, wherein the end effector comprises an ultrasonic end effector.

7. The surgical instrument of claim 1, wherein the end effector comprises a staple cartridge.

8. The surgical instrument of claim 1, further comprising:
a shaft connected to the end effector; and
a handle connected to the shaft.

9. The surgical instrument of claim 8, wherein the handle comprises a lever arm which, when actuated, causes the first and second jaw members to transition from the open position to the closed position, such that the pin of the first jaw member moves from the first lobe to the second lobe of the multi-lobed cam slot.

10. The surgical instrument of claim 1, wherein the second jaw member comprises:
a moveable tissue-contacting portion; and
a thermally-controlled spring adjacent to the tissue-contacting portion.

11. The surgical instrument of claim 10, wherein the thermally-controlled spring comprises a temperature-dependent, two-way memory effect, shape memory material.

12. The surgical instrument of claim 11, wherein the shape memory material comprises a shape memory alloy.

13. The surgical instrument of claim 12, wherein the shape memory alloy comprises an alloy selected from the group consisting of a copper-zinc-aluminum-nickel alloy, a copper-aluminum-nickel alloy, and a nickel-titanium alloy.

14. The surgical instrument of claim 11, wherein the thermally-controlled spring is transitionable between a contracted state and an expanded state, wherein the thermally-controlled spring urges the moveable tissue-contacting portion in a direction toward the first jaw member when the first and second jaw members are in the closed position and the thermally-controlled spring is in the expanded state.

15. The surgical instrument of claim 14, further comprising:
a shaft connected to the end effector; and
a handle connected to the shaft.

16. The surgical instrument of claim 15, wherein the handle comprises a lever arm which, when actuated, causes the first and second jaw members to transition from the open position to the closed position, such that the pin of the first jaw member moves from the first lobe to the second lobe of the multi-lobed cam slot.

* * * * *